(12) United States Patent
Flaherty

(10) Patent No.: US 6,749,587 B2
(45) Date of Patent: Jun. 15, 2004

(54) MODULAR INFUSION DEVICE AND METHOD

(75) Inventor: J. Christopher Flaherty, Topsfield, MA (US)

(73) Assignee: Insulet Corporation, Beverly, MA (US)

(*) Notice: Subject to any disclaimer, the term of this patent is extended or adjusted under 35 U.S.C. 154(b) by 114 days.

(21) Appl. No.: 10/081,394

(22) Filed: Feb. 22, 2002

(65) Prior Publication Data
US 2002/0169439 A1 Nov. 14, 2002

Related U.S. Application Data
(60) Provisional application No. 60/270,970, filed on Feb. 22, 2002.

(51) Int. Cl.$^7$ ................................................ A61M 1/00
(52) U.S. Cl. ..................... 604/151; 604/890.1; 604/151
(58) Field of Search ........................... 604/890.1, 891.1, 604/93.01, 892.1, 118, 123, 131, 133, 151, 153, 288.01–288.04, 65–67, 30, 31, 34; 128/DIG. 12; 417/1, 43, 9, 12, 18, 20, 29, 234, 238, 290, 300

(56) References Cited

U.S. PATENT DOCUMENTS

| 306,691 A | 3/1884 | Arai |
| 303,013 A | 8/1884 | Konopka |

(List continued on next page.)

FOREIGN PATENT DOCUMENTS

| DE | 4200595 | 7/1993 |
| DE | 19920896 | 9/2000 |
| EP | 0342947 | 5/1989 |
| EP | 0763369 | 3/1997 |
| EP | 0867196 | 3/1998 |
| EP | 0937475 | 8/1999 |
| WO | WO81/01658 | 6/1981 |
| WO | WO86/06796 | 11/1986 |
| WO | WO98/00193 | 1/1998 |
| WO | WO98/01071 | 1/1998 |
| WO | WO99/10040 | 3/1999 |
| WO | WO99/62576 | 9/1999 |
| WO | WO99/56803 | 11/1999 |
| WO | WO00/10628 | 3/2000 |
| WO | WO00/29047 | 5/2000 |
| WO | WO00/29049 | 5/2000 |
| WO | WO00/30705 | 6/2000 |
| WO | WO00/48112 | 8/2000 |
| WO | WO00/61215 | 10/2000 |
| WO | WO01/5663 | 8/2001 |
| WO | WO01/76684 | 10/2001 |
| WO | WO02/20073 | 3/2002 |
| WO | WO02/26282 | 4/2002 |

OTHER PUBLICATIONS

US 5,954,699, 9/1999, Jost et al. (withdrawn)

Primary Examiner—Brian L. Casler
Assistant Examiner—Cris L. Rodriguez
(74) Attorney, Agent, or Firm—McDermott, Will & Emery

(57) ABSTRACT

A device for delivering fluid including a disposable assembly having an exit port assembly and a metering portion of a dispenser for controlling fluid flow to the exit port assembly, and a reusable assembly having a control portion of the dispenser adapted to control the metering portion of the dispenser upon attachment of the reusable assembly and the disposable assembly, a local processor connected to the dispenser and programmed to cause fluid flow to the exit port assembly through the dispenser based upon flow instructions, and a local wireless communication element connected to the local processor for receiving flow instructions from a remote wireless device. The assemblies are adapted to be removably attached, and a power source is contained in the disposable assembly for providing power to the reusable assembly upon attachment of the reusable assembly and the disposable assembly.

56 Claims, 6 Drawing Sheets

U.S. PATENT DOCUMENTS

| | | |
|---|---|---|
| 315,727 A | 3/1885 | Arai et al. |
| 311,735 A | 10/1885 | Aran et al. |
| 405,524 A | 2/1889 | Falk et al. |
| 3,631,847 A | 1/1972 | Hobbs |
| 3,812,843 A | 5/1974 | Wootten et al. |
| 4,067,000 A | 1/1978 | Carlson |
| 4,108,177 A | 8/1978 | Pistor |
| 4,151,845 A | 5/1979 | Clemens |
| 4,193,397 A | 3/1980 | Tucker et al. |
| 4,211,998 A | 7/1980 | Junginger et al. |
| 4,231,019 A | 10/1980 | Junginger et al. |
| 4,268,150 A | 5/1981 | Chen |
| 4,364,385 A | 12/1982 | Lossef |
| 4,373,527 A | 2/1983 | Fischell |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A * | 12/1985 | Franetzki et al. ............ 604/151 |
| 4,560,979 A | 12/1985 | Rosskopf |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,882,600 A | 11/1989 | Van de Moere |
| 4,886,499 A | 12/1989 | Cirelli et al. |
| 4,898,579 A | 2/1990 | Groshong et al. |
| 4,944,659 A | 7/1990 | Labbe et al. |
| 4,969,874 A | 11/1990 | Michel et al. |
| 4,973,998 A | 11/1990 | Gates |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,178,609 A | 1/1993 | Ishikawa |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,281,202 A | 1/1994 | Weber et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. .............. 128/633 |
| 5,514,096 A | 5/1996 | Hiejima |
| 5,533,389 A | 7/1996 | Kamen et al. |
| 5,545,152 A | 8/1996 | Funderburk et al. |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson |
| 5,800,405 A | 9/1998 | McPhee |
| 5,807,075 A * | 9/1998 | Jacobsen et al. ............ 417/44.2 |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,961,492 A | 10/1999 | Kriesel et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,174,300 B1 | 1/2001 | Kriesel et al. |
| 6,190,359 B1 | 2/2001 | Heruth |
| 6,375,638 B2 | 4/2002 | Nason et al. |
| 6,520,936 B1 | 2/2003 | Mann |
| 6,527,744 B1 | 3/2003 | Kriesel et al. |
| 2002/0040208 A1 * | 4/2002 | Flaherty et al. ........ 604/288.01 |

\* cited by examiner

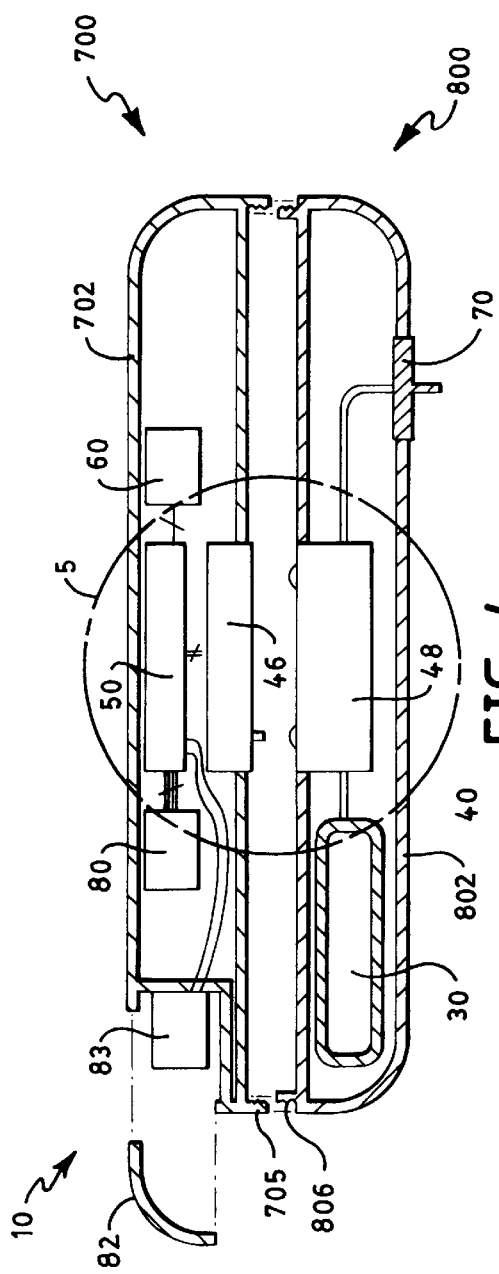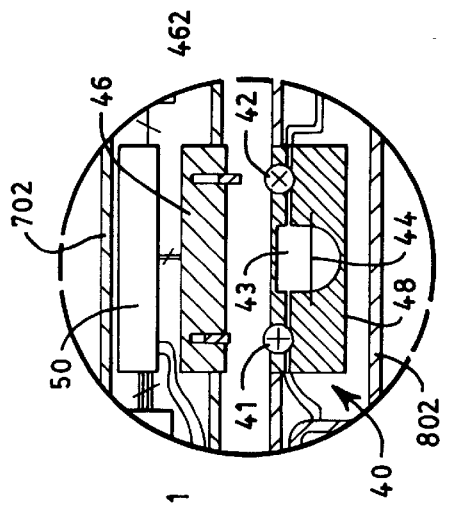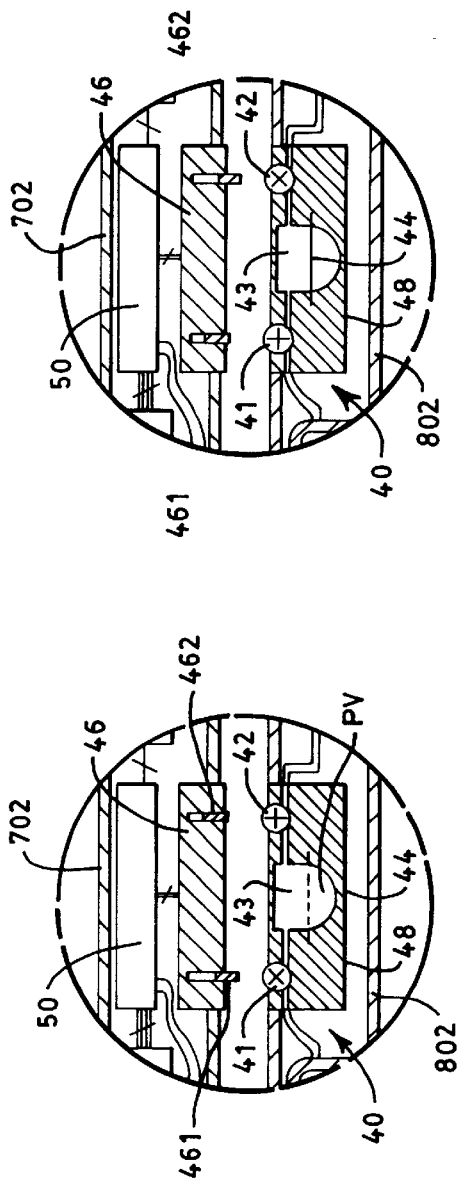

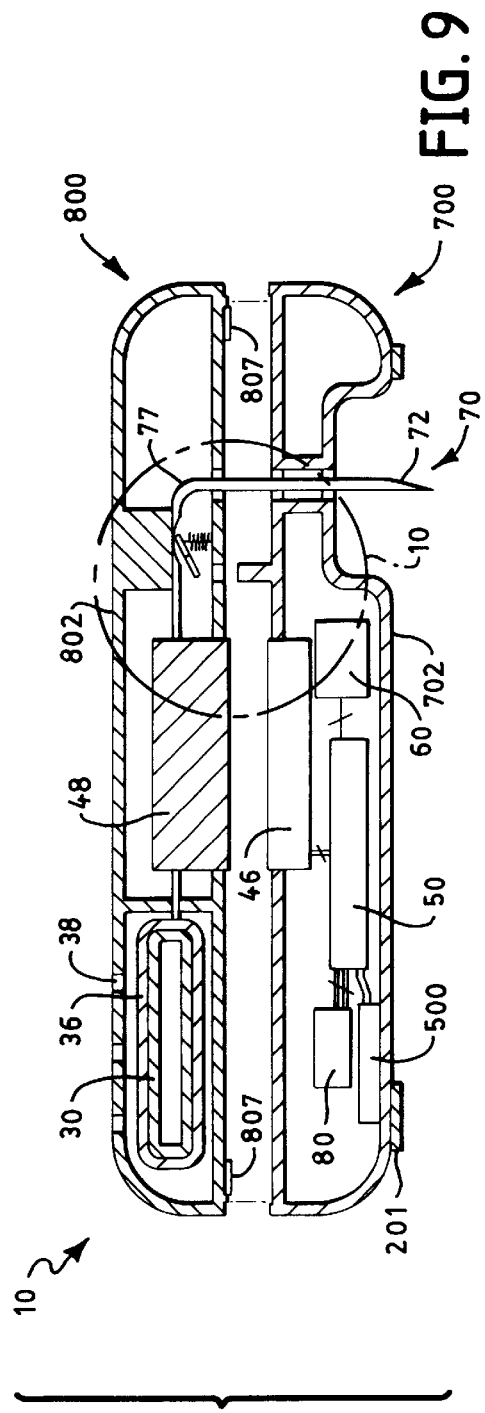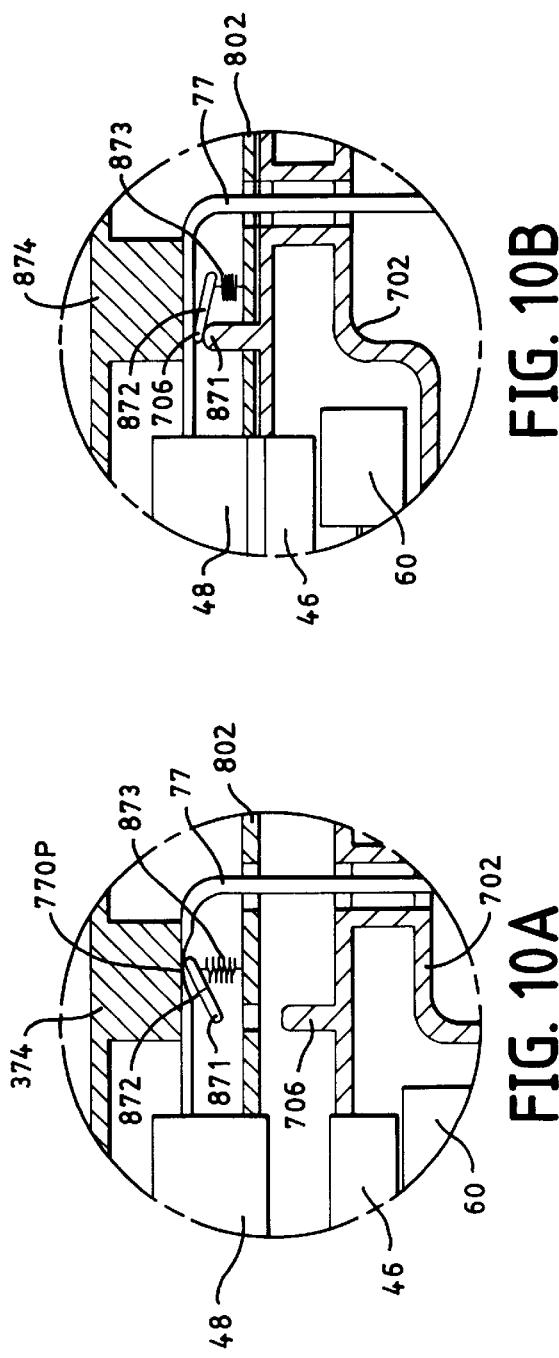

MODULAR INFUSION DEVICE AND METHOD

CROSS-REFERENCE TO RELATED APPLICATIONS

The present application claims priority to provisional U.S. patent application Serial No. 60/270,970, filed on Feb. 22, 2002, which is assigned to the assignee of the present application and incorporated herein by reference. The present application is related to U.S. patent application Ser. No. 09/943,992, filed on Aug. 31, 2001, and entitled DEVICES, SYSTEMS AND METHODS FOR PATIENT INFUSION, which is assigned to the assignee of the present application and incorporated herein by reference.

FIELD OF THE INVENTION

The present invention relates generally to devices for delivering therapeutic fluids and more particularly to small, portable infusion devices and methods that can be used to transcutaneously deliver these fluids safely and simply to a mammalian patient. Even more particularly, the present invention relates disposable and reusable modular components of a, small, portable infusion device.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a, mammalian patient to avoid degradation of the active ingredients caused by the catalytic enzymes in the digestive tract and liver. Delivery of a medicine other than by way of the, intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site-specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge or reservoir, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long-term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, light weight, simple to use alternative for parenteral delivery of liquid medicines.

In response, the applicant of the present application provided a small, low cost, lightweight, easy to use device for delivering liquid medicines to a patient, which is described in co-pending U.S. application Ser. No. 09/943, 992, filed on Aug. 31, 2001. The device includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

What is still desired are new and improved devices for delivering fluid to a patient. Preferably, the fluid delivery devices will be simple in design, and inexpensive and easy to manufacture, to further reduce the size, complexity and costs of the devices, such that the devices or portions thereof lend themselves to being small and disposable in nature.

In addition, the fluid delivery devices will preferably include combinations of disposable and reusable modular components in an effort to further reduce the costs of such devices.

SUMMARY OF THE INVENTION

The applicant has determined that a sophisticated ambulatory infusion device that can be programmed to reliably deliver variable flow profiles of liquid medications, yet is small, lightweight and low cost, is needed. Avoiding the general upkeep and maintenance required by expensive, long-term use devices is necessary for broader acceptance of ambulatory infusion therapy. Smaller and lighter devices are easier to carry and are more comfortable for the patient even allowing the device to attach with adhesive to the patient's skin similar to a transdermal patch.

An inexpensive device allows greater flexibility in prescribing the device for use by reducing the financial burden on healthcare insurance providers, hospitals and patient care centers as well as patients themselves. In addition, low cost devices make it more practical for a patient to have one or more replacement devices readily available. If the primary device is lost or becomes dysfunctional, availability of the replacement eliminates costly expedited repair and avoids periods of discontinued ambulatory therapy.

The present invention, therefore, provides a small, lightweight and low cost fluid delivery device capable of adjustable and programmable fluid delivery includes a housing that surrounds a reservoir chamber. In fluid communication with the reservoir chamber is a dispenser for dispensing the fluid from the reservoir in finite amounts. The dispenser is controlled by an electronic microcontroller (referred to as the "local processor") of the fluid delivery device. The fluid delivery device further includes a communication element that receives information from a remote control device not mechanically attached to the fluid delivery device of the present invention. Also included is an exit port assembly in fluid communication with the dispenser from which the liquid medication exits the fluid delivery device and enters the body of a mammalian patient transcutaneously.

The types of liquids that could be delivered by the fluid delivery device of the present invention include but are not limited to: insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device of the present invention might be used to treat are diabetes, cardiovascular disease, pain, chronic pain, cancer, AIDS, neurological diseases, Alzheimer's Disease, ALS, Hepatitis, Parkinson's Disease or spasticity.

The housing of the fluid delivery device is preferably free of electromechanical elements, such as switches or buttons, that the patient would press to program or alter the programming of the fluid delivery device. The primary interface between the fluid delivery device and the user is via the remote control device.

In a particular embodiment of the present invention, the device for delivering fluid includes a disposable assembly having an exit port assembly, a metering portion of a dispenser for controlling fluid flow to the exit port assembly, and a housing containing the exit port assembly and the metering portion of the dispenser. The device also includes a reusable assembly having a control portion of the dispenser adapted to control the metering portion of the dispenser upon attachment of the reusable assembly and the disposable assembly, a local processor connected to the dispenser and programmed to cause fluid flow to the exit port assembly through the dispenser based upon flow instructions, a local wireless communication element connected to the local processor for receiving flow instructions from a remote wireless device, and a housing containing the control portion of the dispenser, the controller and the local wireless communication element.

The housings of the disposable assembly and the reusable assembly are adapted to be removably attached, and a power source is contained in the disposable assembly for providing power to the reusable assembly upon attachment of the reusable assembly and the disposable assembly.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 4 is an exploded sectional side view of an additional embodiment of the modular fluid delivery device of the present invention;

FIGS. 5a and 5b are sectional views of the portions of the fluid delivery device contained in circle 5 of FIG. 4, illustrating operation of a dispenser of the device;

FIG. 9 is an exploded sectional side view of a further embodiment of the modular fluid delivery device of the present invention;

FIGS. 10a and 10b are sectional views of the portions of the fluid delivery device contained in circle 10 of FIG. 9, illustrating operation of a fluid release mechanism of the device;

Like reference characters designate identical or corresponding components and units throughout the several views.

DETAILED DESCRIPTION OF THE EXEMPLARY EMBODIMENTS

Figure 1:
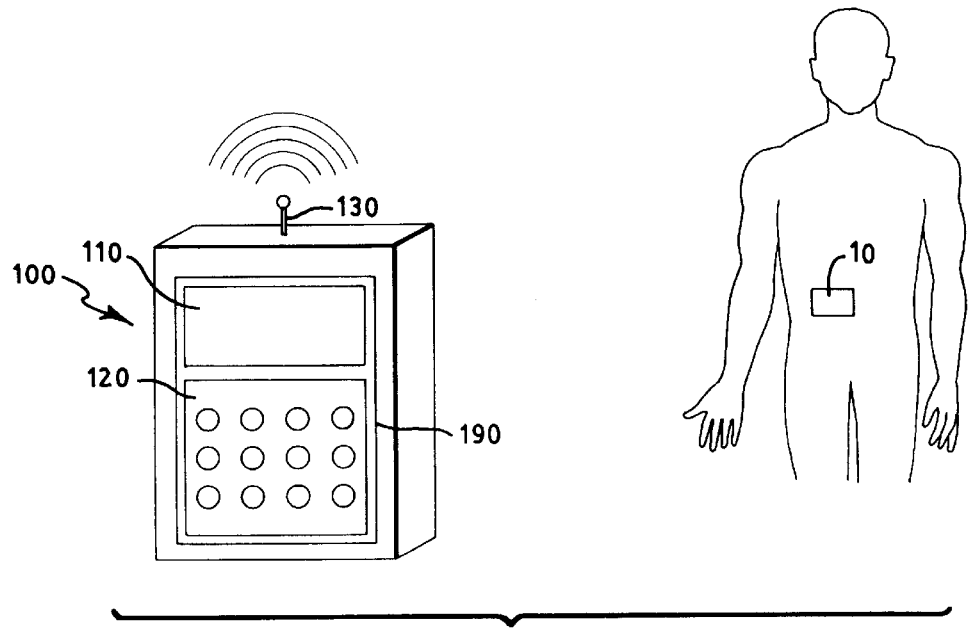
FIG. 1 is a perspective view of an exemplary embodiment of a system constructed in accordance with the present invention and including a fluid delivery device shown secured on a patient, and a remote control device for use with the fluid delivery device (the remote control device being enlarged with respect to the patient and the fluid delivery device for purposes of illustration)
Figure 2:
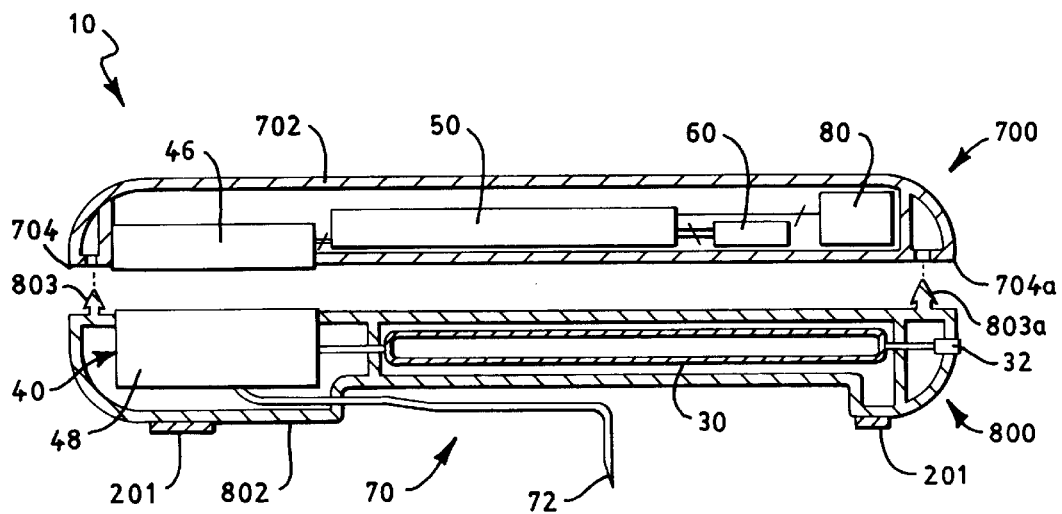
FIG. 2 is an exploded, sectional side view of the fluid delivery device of FIG. 1, showing reusable and disposable modular components of the device.

Referring first to FIGS. 1 and 2, there is illustrated an exemplary embodiment of a fluid delivery device 10 constructed in accordance with the present invention. The types of liquids that can be delivered by the fluid delivery device of the present invention include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device of the present invention might be used to treat include, but are not limited to, diabetes, cardiovascular disease, pain, chronic pain, cancer, AidentificationS, neurological diseases, Alzheimer's Disease, ALS, Hepatitis, Parkinson's Disease or spasticity.

Referring just to FIG. 2, the present invention provides an improved fluid delivery device 10, wherein the components of the device 10 are provided in at least two assemblies 700, 800 which are assembled together for use, and wherein one of the assemblies 800 is disposable and the other of the assemblies 700 is reusable. The reusable assembly 700 is removably attachable to the disposable assembly 800. The reusable assembly 700 is designed to include the more costly components of fluid delivery device 10. Preferably the fluid delivery device 10, with assemblies attached, is small, with a cross-sectional area about the size of a credit card and a thickness less than one inch.

Referring to FIG. 2, the device 10 generally includes an exit port assembly 70 including a transcutaneous patient access tool, such as a rigid or flexible cannula 72 for penetrating the skin of a patient, a dispenser 40 for causing fluid from a reservoir 30 to flow to the exit port assembly 70, and a processor or electronic microcontroller (hereinafter referred to as the "local" processor) 50 connected to the dispenser 40. The local processor 50 can include various components, such as a microprocessor, an electronic memory, an electronic clock oscillator, an analog to digital converter and a multiplexer.

The local processor 50 is programmed to cause a flow of fluid to the exit port assembly 70 based on flow instructions from a separate, remote control device 100, an example of which is shown in FIG. 1. Referring also to FIG. 2, the fluid delivery device 10 further includes a wireless receiver 60 connected to the local processor 50 for receiving the flow instructions from the separate, remote control device 100 and delivering the flow instructions to the local processor. The disposable assembly 800 includes a housing 802 and the reusable assembly 700 includes a housing 702, and the housings 702, 802 contain the exit port assembly 70, the reservoir 30, the dispenser 40, the local processor 50, and the wireless receiver 60.

As shown, the housings 702, 802 are free of user input components for providing flow instructions to the local processor 50, such as electromechanical switches or buttons on outer surfaces of the housings 702, 802, or interfaces otherwise accessible to a user to adjust the programmed flow rate through the local processor 50. The lack of user input components allows the size, complexity and costs of the device 10 to be substantially reduced so that the device 10 lends itself to being small and disposable in nature.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 130, shown in FIG. 1 as being external to the device 100.

Referring to FIGS. 1 and 2, the remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element 60 comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser 40 at the needed time intervals.

In the exemplary embodiment of FIG. 2, the device 10 includes a power supply 80, such as a battery or capacitor, for supplying power to the local processor 50 and other components of the device. The power supply 80 is preferably integrated into the fluid delivery device 10, but can be provided as replaceable, e.g., a replaceable battery.

Although not shown, the device can include sensors or transducers such as a reservoir volume transducer or a reservoir pressure transducer, for transmitting information to the local processor 50 to indicate how and when to activate the dispenser 40, or to indicate other parameters determining flow, pump flow path prime condition, blockage in flow path, contact sensors, rotary motion or other motion indicators, as well as conditions such as the reservoir 30 being empty or leaking, or the dispensing of too much or too little fluid from the reservoir, etc.

The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 30 may be pre-filled by the device manufacturer or a cooperating drug manufacturer, or may include external filling means, such as a fill port 32 having needle insertion septum or a Luer connector, for example. In addition, the device 10 can be provided with a removable reservoir. The cross-sectional area of the reservoir 30 is preferably more than half the cross-sectional area of the housing 802, in order to reduce the required thickness of the housing 802.

As shown, the device 10 also includes an adhesive layer 201 on the outer surface of the disposable housing 802 for securing the device 10 directly to the skin of a patient. The adhesive layer 201 is preferably provided in a continuous ring encircling the exit port assembly 70 in order to provide a protective seal around skin penetrated by the cannula 72. The housings 702, 802 can each be made from flexible material, or can be provided with flexible hinged sections that allow the fluid delivery device 10 to flex during patient movement to prevent detachment and aid in patient comfort.

The dispenser 40 is connected in fluid communication with the reservoir 30, as shown in FIG. 2, and controlled by the local processor 50, which includes electronic programming, controls and circuitry to allow sophisticated fluid delivery programming and control of the dispenser 40. When the device 10 is provided with a pressurized reservoir 30 (i.e., fluid maintained within the reservoir at a pressure above atmospheric), the dispenser 40 is configured to act as a metering device, allowing pulses of fluid to pass from the pressurized reservoir 30, through the dispenser 40, to the exit port assembly 70 at atmospheric pressure. When the device 10 is provided with a non-pressurized reservoir 30, the dispenser 40 is configured to create a driving or pumping force on the fluid passing therethrough.

In the embodiment of the delivery device 10 of the present invention shown in FIG. 2, the reusable assembly 700 contains the local controller 50, the communication element 60, the battery 80, and a meter control portion 46 of the dispenser 40. The disposable assembly 800 contains the reservoir 30, the fill port 32, the exit port assembly 70 and a metering portion 48 of the dispenser 40. The meter control portion and the metering portions 46, 48 of the dispenser 40 are adapted and positioned to mate upon attachment of the assemblies 700, 800.

The meter control portion 46 includes actuators such as solenoids, piezo actuators, magnetic actuators, thermal generators or other mechanisms to generate, direct or redirect a force, temperature gradient, electromagnetic field or other medium for controlling the metering portion 48 of the dispenser 40. The metering portion 48 directly controls fluid flow between the reservoir 30 and the exit port assembly 70. If the reservoir 30 is maintained at ambient pressure, the metering portion 48 may include a rotary peristaltic head, linear peristaltic mechanism, electromagnetic fluid propulsion, a displacement pump, or other means for moving fluid from the reservoir 30 to the exit port assembly 70. Such propulsion means may be accomplished by a rotary peristaltic head included in the metering portion 48 that is driven by a motor drive which is integrated into the meter control portion 46. If the reservoir 30 is pressurized, the metering portion 48 may simply control flow, and not to propel the fluid. The reservoir 30 may be included in a sealed compartment, and pressurized gas provide the driving force, or the reservoir may be in contact with a force generating member such as a spring, a separate elastomeric structure, or a cantilever beam attached to the housing 802 of the disposable assembly 800.

The reusable assembly 700 includes attachment means for mechanically attaching to the disposable assembly 800 such as connecting hole 704 and large connecting hole 704A which are holes through the housing 702. Each hole is placed to accept a projecting member, such as small connecting projection 803, which mates with a small connecting hole 704, and a large connecting projection 803A which mates with a large connecting hole 704A. By varying the size or geometric shape of the connection projections and mating holes, a specific alignment can be created in an otherwise symmetric device shape, such as a round configuration. The aligning members may be located at the geometric center of either or both assemblies.

The small connecting projection 803 and the large connecting projection 803A include an arrow-shaped profile wherein a portion, or lever arm, of the arrow extends beyond the diameter of the corresponding receiving hole. The lever arm of the arrow larger portion can bend back to allow each projecting member to pass through the receiving hole after which the lever arm snaps back, therefore locking the reusable assembly 700 to the disposable assembly 800. This particular arrow-shaped geometry requires large forces to be used to detach the reusable assembly 700 from the disposable assembly 800, such force to bend the lever arms of the arrow in the reverse direction, or to actually break the lever arms off. Alternative designs and geometries described below are more suitable for fluid delivery devices requiring subsequent detachment after initial attachment, the preferred use. A bulbous construction at the end of the projecting members, for example, with each projecting member bulbous member with a diameter slightly larger than the diameter of each receiving hole, could replace the arrow shaped constructions. Moderate amounts of force would be required to snap the two assemblies together as well as to detach them after attachment.

Alternatively, the projecting members could be located on the reusable assembly 700 and the receiving holes could be located on the disposable assembly 800. However, in cases where the reusable assembly 700 may be used with numerous disposable assemblies 800, it is desirable for the more fragile projecting members to be located on the disposable assembly 800, since the projecting members may be prone to breaking off after attachment and detachment. Alternatively, projecting members could be included on both assemblies, and corresponding receiving holes or surfaces included on the opposite assembly.

Numerous other shapes of projecting members, and correspondingly shaped receiving holes could be substituted for what has been described above without departing from the scope of the invention. Various geometries of attachable and subsequently detachable snap fit designs are known to those of skill in the art. Alternatively, limited force glues could be employed, matched threads on each assembly could be incorporated, or various other snap fit mechanisms could be integrated. Some alternative attachment means are described in the embodiments founds herebelow. In the case where threads are employed and the two assemblies screw together, a means of prevented unintended detachment could be incorporated, such as that used in child-proof pill bottles.

The housing adhesive layer 201 can include standard biocompatible glues such as those used in common band-aids, and may include a protective covering, not shown, to avoid the adhesive sticking to unwanted objects prior to attachment to the skin of the patient. In FIG. 1, housing adhesive layer 201 is attached to disposable assembly 800 such that disposable assemble would be in closest proximity to the patient's skin, with reusable assembly 700 located a distance away from the body. In certain applications, it may be desirable to have housing adhesive layer 201 attached to the reusable assembly 700 such that reusable assembly 700 is in closest proximity to the patient's skin, and disposable assembly 800 located a distance away from the body. Since reservoir 30 is contained within disposable assembly 800, it may be desirable to avoid direct contact of disposable assembly 800 with the patient's body to reduce heat transfer to reservoir 30 which may degrade the therapeutic fluid contained therein. After a specific disposable assembly 800 has reached it's limited life, a second disposable assembly 800 may be attached to reusable assembly 700 without detaching from the skin of the patient. If detachment is desired, the reusable assembly 700 could be detached from the skin of the patient, the disposable assembly 800 detached, if not detached already, a second disposable assembly 800 attached, and the combined assemblies attached at the same or another location. The exit port assembly 70 could be inserted transcutaneously into the patient either before or after attachment of the combined assemblies to the patient's skin. The housing adhesive layer 201, when attached to the reusable assembly 700, may be user replaceable in conditions where the adhesive has lost its gripping force.

The method of attaching either the disposable assembly 800 or the reusable assembly 700 to the patient's skin can be accomplished prior to attaching either assembly to each other, or after the two assemblies have been attached to each other. The skin penetrating cannula 72 can be introduced through the patient's skin prior to attachment of either or both assemblies to the patient's skin, at the same time as either or both assemblies is attached to the patient's skin, or after either or both assemblies are attached to the patient's skin. Simultaneous puncturing of the patient's skin by the penetrating cannula 72 and attachment of either or both assemblies may be preferred to simplify attachment and reduce pain of transcutaneous puncturing.

Depending upon geometric construction of the disposable assembly 800 and reusable assembly 700, both assemblies may include means of fixedly attaching the combined assembly to the patient's skin, not shown. Such a geometric layout may allow both assemblies to be in near proximity to the patient's skin, also not shown, in a side by side configuration. The adhesive segments attached may be continuous or discontinuous, may include coverings to be removed prior to attachment, and may include multiple adhesive layers to allow removal of a single layer to expose a new, unused segment.

In addition to the connecting means, such as the small connecting projection 803 and the connecting hole 704, the reusable assembly 700 and the disposable assembly 800 may include means of aligning the two assemblies. Alignment projecting members could have specific sizes and shapes which mate with similarly sized and shaped mating holes or surfaces to facilitate proper alignment of the reusable assembly 700 and the disposable assembly 800. These alignment projections and receiving holes or surfaces may be of added value with the other forms of attachment means such as glues and threads, all not shown. Projecting alignment members may be included on either or both the disposable assembly 800 and the reusable assembly 700, with mating receiving holes or surfaces on the corresponding assembly.

The housings 702, 802 can be constructed of the same or different materials. For example, the housing 702 can be constructed of a more durable material to support longer intended life, while the housing 802 can be constructed of a softer or otherwise less durable material. In addition, the housing 802 of the disposable assembly may be constructed of a biodegradable material. Preferably, both of the housings 802, 702 are constructed of biodegradable, recyclable or other environmentally friendly materials.

One or both of the housings 702, 802 can be constructed of a soft or flexible material, such as injection molded plastics and elastomers, chosen to provide comfort to the patient while protecting components from damage. The corresponding housing, which is preferable located on top of its counterpart, may be constructed of a more durable or less flexible material, to protect the combined assembly from damage during patient ambulation or other movement. The housings 702, 802 may include hinged sections, not shown, to allow flexing of the attached assemblies when worn. The materials of construction of the fluid path are chosen to include materials that are both biocompatible and compatible with the therapeutic fluid to be infused. Materials such as silicone, polyvinylchloride, polyethylene, nylon and other medical grade materials are common to infusion devices.

Either or both the housing 802 and housing 702 may include compartments surrounding one or more components. The reservoir 30 may be surrounded by a sealed compartment which pressurized gas to pressurize the reservoir. The electronic microcontroller 50 may include a shielded compartment to protect itself from external electronic interference or prevent transmitting unwanted electronic interference to other devices. The electronic microcontroller 50 or power supply 80 may be included in a watertight compartment to prevent discharge of power, creation of discharging contaminated pathways, or other purposes. Compartments may be created to protect components from thermal effects, electromagnetic effects, mechanical, fluid or other damage, or for various other purposes.

The geometric structure of the reusable assembly 700 and the disposable assembly 800 can take various shapes such as cylindrical or rectangular. The inner components are laid out to minimize overall size, and the outer surface can be contoured to be comfortable when worn attached to the body via adhesive attachment means, not shown.

Both the reusable assembly 700 and the disposable assembly 800 can include their own power supplies such as batteries or capacitors, which may be permanently integrated or user replaceable. Electronic mating connections may be included between the two assemblies such that power included in one assembly can be utilized by the other assembly. In a preferred embodiment, the reusable assembly 700 includes the power supply 80, and the power supply is permanently integrated power supply 80, such as a capacitor. In another embodiment, not shown, the disposable assembly 800 also includes a permanently integrated power supply, such that a user never has to buy separate batteries for the device 10.

The power supply in the reusable assembly 700, potentially a capacitor, can be charged by the battery in the disposable assembly 800 when the two assemblies are attached to one another. The reusable assembly 700 can use power from its internal power supply whenever not attached to a disposable assembly 800, such as to support electronic memory retention or to transmit information to the remote controller 100, but when attached, utilize power from a power supply integrated into the reusable assembly 700. In this configuration, power usage of the reusable assembly 700 is extremely minimal, and the power supplied to the system by the power supply in the disposable assembly 800 is replenished whenever a new disposable assembly 800 is employed. The power supply of the disposable assembly 800 may be chosen to supply power for a limited amount of infusion, limited life, or other limitation lending itself to a predetermined disposability.

Instead of the integrated skin penetrating cannula 72, the disposable assembly 800 may include an exit port assembly 70 that includes a standard attachment, such as a luer connector, that can be attached to a separate transcutaneous infusion set. Such an infusion set can be supplied with the system, or could be obtained separately. A typical kit arrangement for the system could include a multiple of disposable assemblies 800, a lesser number of reusable assemblies 700, and number of remote controllers 100 equal to or lesser than the number of reusable assembly 700. If the reservoir 30 of disposable assembly 800 is not pre-filled, a number of vials or other containers of therapeutic fluid may also be provided. Such a kit can also be provided with transcutaneous infusion sets if the disposable portions do not include the integrated skin penetrating cannula 72.

Figure 3:
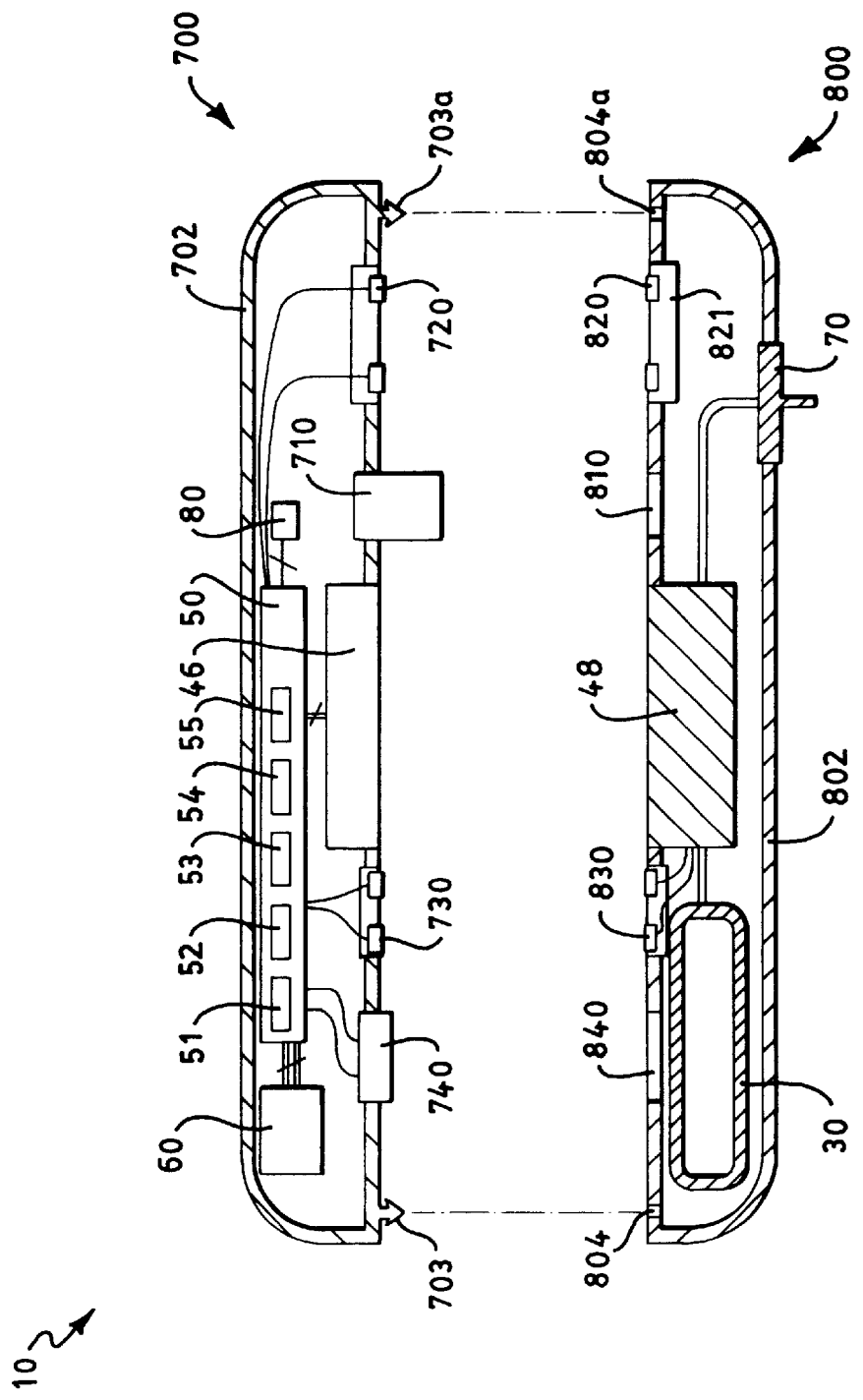
FIG. 3 is an exploded sectional side view of another embodiment of the modular fluid delivery device of the present invention.

FIG. 3 shows another exemplary embodiment of a fluid delivery device 10 constructed in accordance with the present invention. The device of FIG. 3 is similar to the device of FIGS. 1 and 2, such that similar elements have the same reference numeral.

The fluid delivery device 10 of FIG. 3 includes an electronic microcontroller 50 having various components, such as a microprocessor 51, an electronic memory 52, an electronic clock oscillator 53, an analog to digital converter 54 and a multiplexer 55. The microprocessor 51 can be an industry standard microprocessor such as that included in personal computers and various other sophisticated electronic devices, or can be customized utilizing silicon integrated circuit fabrication. The electronic memory 52 can include read only memory, random access memory, writeable memory, programmable memory, electronically erasable memory and other memory. The electronic memory 52 includes one or more software programs of the device 10 that may be preloaded during manufacturing or downloaded after manufacturing, either partially or in full. The electronic clock oscillator 53 provides a repetitive signal to allow the electronic microcontroller 50 to keep track of time, perform operations at certain intervals and otherwise provide a precision counting function. The analog to digital converter 54 converts signals from sensors or other analog output electronic devices to a digital signal for the microprocessor 51 and other electronic components of electronic microcontroller 50. Alternatively or additionally, a digital to analog converter may be incorporated to input a digital signal such as that output by the microprocessor 51 and convert it to an analog signal that can be utilized by an output device, such as an audio transducer or other component that requires an analog input to function. The multiplexer 55 may be included to allow multiple arrays of signals to be output, input or otherwise communicated between any of the electronic components of electronic microcontroller 50. Additional analog and digital electronic circuitry can be included in electronic microcontroller 50 including but not limited to resistors, capacitors, inductors, gate arrays, transistors and other integrated circuits and components.

Various sensors may be included in disposable assembly 800, such as sensors that may be integrated into metering portion 48 to confirm proper flow of fluid or sensors integrated to confirm proper operation of reusable assembly 700. Information from the sensors, in analog or digital electronic form, may be electrically connected to information contact 830 such that when disposable assembly 800 is connected to reusable assembly 700, information is transmitted through information contact 830 to information contact 730 which is aligned to be in contact with information contact 830 when the two assemblies are properly connected. Both the information contact 730 and the information contact 830 include one or more contacts, which may be spring loaded, which mate with a corresponding contact on the other assembly, making an electrical connection when the two assemblies are connected. Electronic signals containing analog, digital or hybrid information can be sent from one assembly to the other via the contacts, in addition, power can be transmitted with similar assemblies. Alternatively, wireless communication means may be included to transmit information from the sensors of disposable assembly 800 to the electronics of reusable assembly 700.

Reusable assembly 700 may include various sensors as well, such as a sensor to verify adequate flow in the disposable assembly 800, such as a sensor assembly 710 that is shown protruding from housing 702 and entering an inner chamber of the disposable assembly 800 via sensor receiving slot 810. The sensor assembly 710 may be an air bubble detector, such as those manufactured by Zevex Corporation, a pressure sensor or pressure transducer, or a flow sensor, all known to those of skill in the art. The sensor assembly may come in close proximity, or even surround a portion of the flow path of the disposable assembly such as a portion of tubing through which all of the fluid flows. The sensors of the reusable assembly 700 may protrude through or make contact with the housing 802 of disposable assembly 800. The sensor assemblies of the reusable assembly 700 may make contact with or surround portions of the fluid path of disposable assembly 800. The sensor assemblies may monitor blockage of flow including an occluded state. The sensor assemblies of reusable assembly 700 may work in conjunction with mating partial or complete sensor assemblies of the disposable assembly 800. The sensor assemblies of reusable assembly 700 may include light generators and photosensors to perform measurements, check the clearance of a specific path, or otherwise gather information regarding one or more parameters of the function of the fluid delivery device 10, specifically a parameter related to fluid flow.

Attached to electronic microcontroller 50 is a power supply 80, such as a battery or capacitor. Power supply 80 may attach to various other components requiring electrical power. In a preferred embodiment, power supply 80 of reusable assembly 700 supplies power for a limited number of functions, such as memory retention, and the majority of power supplied by a power supply included in the disposable assembly 800 which is electrically connected to various components of the reusable assembly 700 when the reusable assembly 700 is attached to the disposable assembly 800.

The disposable assembly 800 of FIG. 3 also includes a power supply, such as a battery 821. The battery may be nickel cadmium, alkaline, lithium and or other battery technology common to miniature handheld devices. In the preferred embodiment, the battery is not user-replaceable, and since the disposable assembly 800 has a limited life, typically less than 7 days, the battery can be rather small. The battery 821 can be attached to a printed circuit board, on which other electrical components, such as sensors, can also be mounted. The battery and printed circuit board may be enclosed or partially enclosed in a sealed compartment to prevent contamination.

The battery 821 includes means of transferring power to the reusable assembly 700 such as a battery contact 820 which mates with a battery contact 720 of the reusable assembly 700. The battery contact 720 may include flexible fingers, or spring loaded conductive material to properly connect with the battery contact 820. Power is only supplied to the reusable assembly 700 from the disposable assembly 800 when the two assemblies are properly attached to one another. The power transmitting means, such as a plug and receptacle not shown, can be used to attach or assist in attaching the two assemblies to each other.

The power from the battery 821 can be used to supply the electronic microcontroller 50, the communication element 60, the meter control portion 46 and other electronic components of the reusable assembly 700 as well as supply power to various electrical components of disposable assembly 800. It may be desirable for power in the reusable assembly 700 to be transferred to electronic components of the disposable assembly in a similar fashion.

Protruding through the housing 702 is a reservoir transducer 740 which extends through a receiving slot 840 in the housing 802, to be in close proximity or in contact with reservoir 30. The reservoir transducer 740 is adapted to sense at least one of various parameters relating to the reservoir 30 including pressure, temperature, air, quantity of fluid or other parameter.

In an alternative embodiment, the reusable assembly 700 may include additional communicating elements or sensors, not shown, which attach to or communicate utilizing wireless technologies with separate instruments, sensors or other types of devices. The communicating elements may be integrated into the reusable assembly 700 such that when the fluid delivery device 10 is placed on the body, the communicating element is in close proximity to a sensor or other device located on or even implanted within the patient. Such a device may be an implanted glucose sensor, and the communicating element of the disposable assembly may be a light emitting device which activates the implanted glucose sensor and receives blood glucose information from it. Such an addition to the system allows for closed loop, or semi closed loop control when dispensing insulin, a key step towards developing an artificial pancreas. The incorporation of the communicating element into the reusable assembly 700 versus the disposable assembly 800 decreases the cost impact since the reusable assembly 700 has a longer duration of use. The diagnostic device or sensor does not have to be implanted, alternatively it could be worn on or near the body, such as a wrist watch device, or may be adhered to the surface of the skin similar to fluid delivery device 10. The communicating element of reusable assembly 700 may include wireless communication means such as RF, or may include direct means of activating or otherwise reading the diagnostic device include transmission of light, heat, or magnetic energies. In addition to blood glucose monitoring, other diagnostic functions that are related to a health condition, specifically those that tie to infusion requirements of the liquid therapeutic, would be beneficial.

FIG. 4 shows an additional exemplary embodiment of a fluid delivery device 10 constructed in accordance with the present invention. The device of FIG. 4 is similar to the device of FIGS. 1 and 2, such that similar elements have the same reference numeral.

The fluid delivery device of FIG. 4 includes a valve assembly 48 located in the disposable portion 800 that is controlled by mechanical actuators 46 included in the reusable portion 700. The metering portion 48 includes two exposed valves 41, 42 which can be activated by external actuators 461, 462.

The disposable assembly 800 includes means of attaching to the reusable assembly 700 such as a cylindrical wall integrated into housing 802 and which includes threads 806 on an outer surface. The threads 806 mate with inner threads 705 that are integrated into the reusable housing 702. The overall device 10 geometry may be a cylinder, however the cylindrical shape is only required in the areas of the threads 705, 806, and a non-cylindrical shape may be employed by the two housings 702, 802 of the two assemblies. In order to assist in properly engaging the threads 705, 806 from the two assemblies 700, 800, an aligning post and receiving hole (not shown) may be incorporated into the geometric center of the thread paths to assist in thread engagement. An aligning post could be included in one assembly, and a properly positioned mating hole included in the other assembly. Other alignment means could alternatively be incorporated.

The threads 705, 806 are designed such that when the two assemblies 700, 800 are screwed together to maximum rotation, the various mating components are located in properly fixed positions. In the device 10 of FIG. 4, the metering portion 48 is located such that its valves 41, 42 are properly aligned with the actuators 461, 462 included in the meter control portion 46. Preferably, the metering portion contains more than one valve to dispense fluid. Redundancy in valves provides a safety feature in that if a particular valve should fail and remain in an open position, the additional valve prevents a free flow of fluid.

Both the metering portion 48 and the meter control portion 46 are located at the geometric centers of the thread assemblies 700, 800 to help align the controlling elements. A configuration that is independent of the number of rotations of the two assemblies relative to each other in the connection process may also be employed, such design including concentric ring shaped actuators, which would be independent of the number of rotations, not shown. Other geometric arrangements, and technologies less sensitive to direct alignment can be incorporated to allow insensitivity to the number of rotations as well.

The reusable assembly 700 includes a secondary power source 83, which also may be a battery or capacitor. In the preferred embodiment, the secondary power source 83 is a consumer available battery, which can be replaced by the user by removing a battery door 82. If the secondary power source 83 is a replaceable battery, the primary power supply 80 is preferably a capacitor or non-replaceable battery which is utilized for low power functions only, such as memory retention.

FIGS. 5a and 5b show an enlarged sectional view of the dispenser 40 of the fluid delivery device 10 including the meter control portion 46 and the metering portion 48. Metering portion 48 includes the inlet valve 41 and the outlet valve 42, which are both normally closed. The inlet valve 41 is proximal to an accumulating chamber 43 which includes a flexible membrane 44. FIG. 5a depicts the accumulator membrane 44 in its expanded state, and a dotted line shows accumulator membrane in its unexpanded condition. The equilibrium position of the accumulator membrane 44 shown by dotted line in FIG. 5a is shown with a solid line in FIG. 5b. A specific pulse volume "PV" of fluid is defined by the volume displaced when the accumulator membrane moves from its fully expanded to equilibrium conditions. Pulse volume PV is determined by the cavity 43 into which accumulator membrane 44 expands. The metering portion 48 is designed to specifically define the volume of pulse volume PV. For diabetes applications wherein typical concentrations of insulin are 100 units per milliliter, a pulse volume of between 0.1 microliter and 5 microliters is acceptable, while a preferred pulse volume is equal to about 2 microliters. Higher concentrations of insulin may become available which can reduce the required size of the reservoir 30 and thus reduce the overall size of the fluid delivery device 10. The pulse volume PV may also need to be reduced to accommodate higher concentrations of insulin and other high concentration liquid medications.

A vent may be included behind the accumulator membrane 44, not shown, to allow air to enter the accumulator 43 when the membrane 44 contracts and escape when the membrane 44 expands. The configuration of FIGS. 4, 5a and 5b assumes that the fluid in reservoir 30 is pressurized above atmospheric pressure, such as by a pressurized chamber, self-contracting reservoir, or other pressurization means. When the inlet valve 41 is opened, maintaining outlet valve 42 closed, the accumulator membrane 44 expands, increasing the fluid volume of accumulator 43 by the pulse volume PV. After a fixed period of time allowed for complete expansion, the inlet valve 41 is closed. The outlet valve 42 can then be opened, allowing the pulse volume PV to exit the accumulator 43 when the membrane 44 contracts. The membrane 44 is constructed of an elastic material under tension to properly expel the fluid. After a fixed period of time, enough to allow discharge of pulse volume PV for a range of acceptable back pressures, the outlet valve 42 is closed and the cycle is repeated to deliver volumes of fluid equal to the pulse volume PV.

The inlet valve 41 and the outlet valve 42 are actuated by the linear actuators 461, 462 included in the metering control portion 46 of the reusable assembly 700. The inlet valve 41 is activated by the first actuator 461 and the outlet valve 42 is activated by the second actuator 462. Each actuator may be a linear solenoid actuator, piezo actuator, or other electrically controlled actuator.

Figure 6:
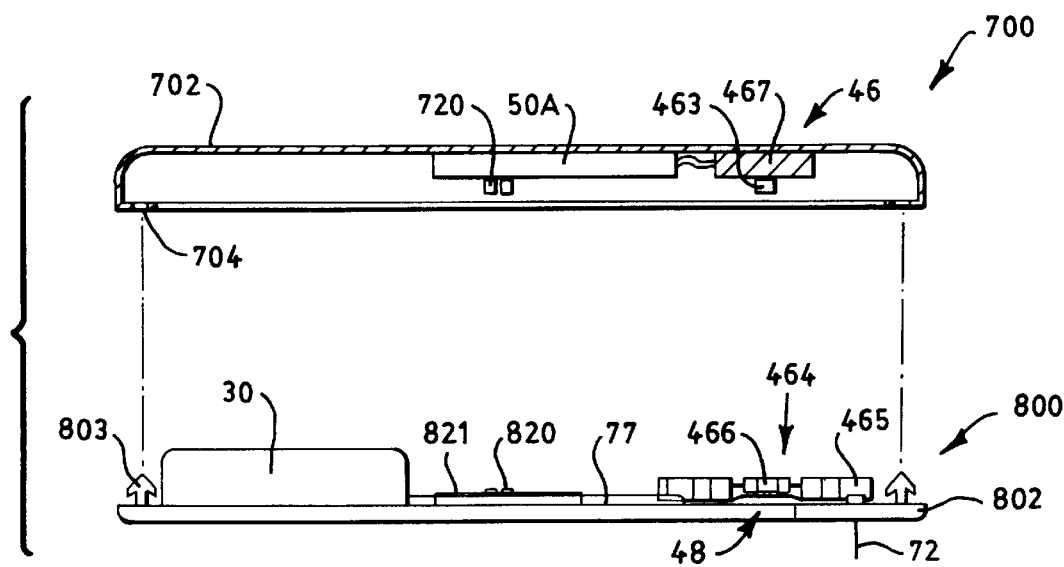
FIG. 6 is an exploded side elevation view, partially in section, of still another embodiment of the modular fluid delivery device of the present invention.

FIG. 6 shows an additional exemplary embodiment of a fluid delivery device 10 constructed in accordance with the present invention. The device of FIG. 6 is similar to the device of FIGS. 1 and 2, such that similar elements have the same reference numeral.

The reusable assembly 700 of the device 10 of FIG. 6 includes an electronic assembly 50A. The electronic assembly is similar to the controller 50 of FIGS. 1 and 2 but also includes means, such as battery contacts 720, for electrically connecting to a power supply 821 of the disposable assembly 800. When the two assemblies 700, 800 are connected, the battery contact 720 of the electronic assembly 50A makes physical contact with a battery contact 820 of the power supply 821. Either or both sets of contacts may be spring-loaded to aid in maintaining contact. The battery 821 is preferably an integrated electrochemical battery not replaceable by a user.

The meter control portion 46 of the reusable assembly 700 includes a rotational drive element 467, which may be an electrically driven rotational motor such as a piezo, stepper or dc motor. Alternatively, the rotational drive element 467 may be a spring driven motor, with electrical actuators determining the specific amount of rotation to be delivered. An actuator in the form of a drive shaft 463 is mechanically attached to the rotational drive element 467 such that when the metering control actuator 463 rotates, the rotational drive element 467 rotates as well. A gear reduction or expansion element may be included, or the drive ratio may be fixed at 1 to 1. The rotational drive element 467 has a shape to allow keyed entry and frictional engagement with one or more components of the metering portion 48 of the disposable assembly 800.

Figure 7:
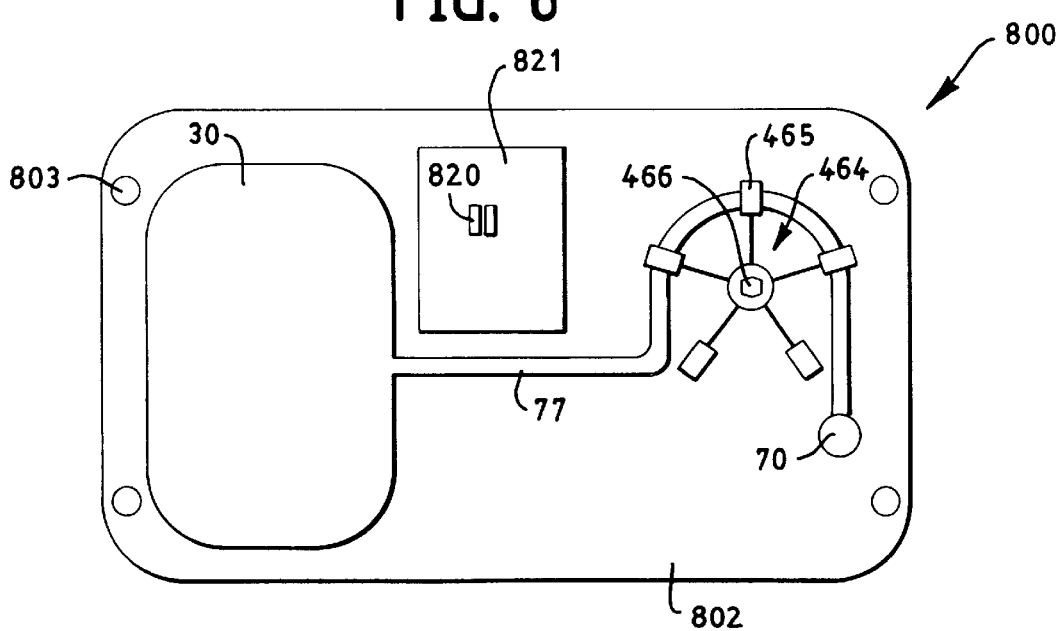
FIG. 7 is a top plan view of a disposable module of the device of FIG. 6.

As shown also in FIG. 7, the metering portion 48 of the disposable assembly 800 includes a rotary peristaltic head which, when rotated, can propel fixed amounts of fluid through a portion of tubing. The metering portion 48 includes a system of attached rollers, rotating roller assembly 464. At the geometric center of rotating roller assembly 464 is keyed receiving hole 466 which mates with metering control actuator 463 of meter control portion 46 of reusable assembly 700. When the disposable assembly 800 and reusable assembly 700 are attached utilizing small connecting projection 803 and connecting hole 704, metering control actuator 463 passes through and is mechanically engaged with keyed receiving hole 466 such that when rotational drive element 467 rotates, equivalent rotations occur with rotating roller assembly 464. Included in rotating roller assembly 464 are multiple rollers, peristaltic roller 465. Each roller is connected to a central hub which is rotationally mounted to a portion of housing 802, and includes, at its geometric center, keyed receiving hole 466. Each peristaltic roller 465 is positioned in contact with a portion of fluid transport tube 77, which is part of the fluid path of the disposable assembly 800, connected at its input to reservoir 30, containing the therapeutic fluid.

Figure 8:
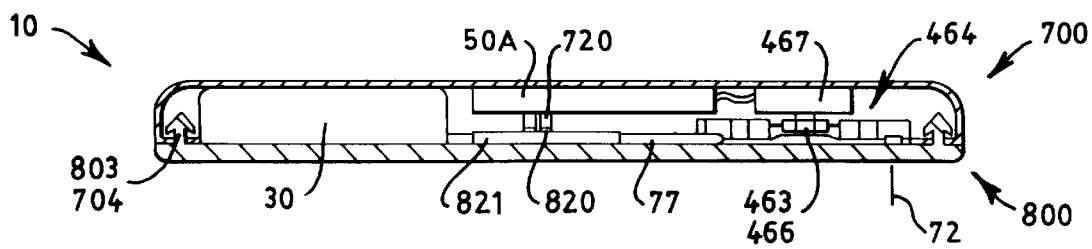
FIG. 8 is a sectional side view of the device of FIG. 6.

Also shown in FIG. 8, the metering control actuator 463 mechanically engages the keyed receiving hole 466 when the assemblies 700, 800 are attached. When rotational drive element 467 rotates, as controlled by electronics assembly 50A based on programming from remote controller, the roller assembly 464 rotates to cause a specific amount of fluid to be pulled from reservoir 30, via fluid transport tube 77, and exit fluid delivery device 10 via skin penetrating cannula 72. The rotary peristaltic mechanism of the disposable assembly 800 of FIGS. 6 through 8 creates fluid propulsion forces, therefore it does not necessarily require the fluid in reservoir 30 to be pressurized.

In order to minimize the overall size of the fluid delivery device 10, particularly the height of the device, components are suitably arranged and allowed to protrude from one assembly into the other. For example, as shown in FIG. 8, clearance is provided in the reusable assembly 700 for the reservoir 30 of the disposable portion 800 to protrude therein.

The disposable portion of the device of FIGS. 6 through 8 is also provided with its own integrated power supply 821. The electronic assembly 50A of the reusable assembly 700 is electrically attached to a battery contact 720, which contacts a battery contact 820 of the disposable assembly 800 to make an electrical connection between the electronics of the reusable assembly 700 and the battery 821 of the disposable assembly 800.

FIG. 9 shows a further exemplary embodiment of a fluid delivery device 10 constructed in accordance with the present invention. The device of FIG. 9 is similar to the device of FIGS. 1 and 2, such that similar elements have the same reference numeral.

In the disposable assembly 800 of the device 10 of FIG. 9, the area of the housing 802 adjacent the reservoir 30 includes vent holes 38 that allow venting to prevent excessive temperature rise of the fluid in the reservoir. Although not shown, the area of the housing 802 that surrounds the reservoir 30 can also be transparent for allowing a visual inspection of the reservoir 30. The transparent portion of the housing 802 can be manufactured with clear plastics or other clear materials. Alternatively, the entire housing 802 may be transparent, allowing the user to visualize all internal components.

Since the disposable assembly 800 of FIG. 6 is located on the top of the fluid delivery device 10, i.e. on top of reusable assembly 700, the reservoir is spaced from the patient's body to further reduce the likelihood of overheating of the fluid in the reservoir 30.

The outlet port 70 includes a compressible fluid transport tube 77, made of a medical grade material such as medical grade silicone or polyvinyl chloride. As shown in FIG. 6, the exit port assembly 70 passes through a hole located in the reusable assembly 700 such that the distal tip 72 of exit port assembly 70 can transcutaneously enter the patient even though the disposable assembly 800 is located on top of the reusable assembly 700.

The disposable assembly 800 and the reusable assembly 700 of FIG. 9 are removably secured together with a continuous adhesive strip 807. The adhesive strip 807 is permanently attached to the disposable housing 802 and provides temporary, yet secure attachment of the disposable assembly 800 to the reusable assembly 700. The reusable assembly 700 includes a smooth mating surface along the housing 702 to contact the adhesive strip 807. Alternatively or additionally, an adhesive means can be included on the reusable assembly 700 as well, to assist in mechanical connection of the two assemblies 700, 800, or alternatively, the adhesive means can be a separate component applied to either or both assemblies 700, 800 just prior to attachment.

Attached to the electronic microcontroller 50 is a data communication assembly (DCA) 500. The DCA 500 is a means of obtaining diagnostic information from a separate device or sensor, or to directly interpret or obtain diagnostic information from the patient's body or a substance that has been removed from the patient's body. The information received or generated by the DCA 500 is input into the electronic memory of electronic microcontroller 50. The information can be sent to the remote controller 100 via communication element 60 and no further use of the information employed. Alternatively, the programming of electronic microcontroller 50 or the internal programming of remote controller 100 can calculate, interpret, modify, or otherwise use or process the information for a secondary function. The secondary function could be to simply report the processed data, or could be used to modify the programming of fluid delivery device 10. The modification may include user required intervention to approve the change, or may simply modify automatically.

A preferred use of the DCA 500 may be as a glucose measurement device, wherein when fluid delivery device 10 is attached to the patient's body, the DCA 500 is proximate to an implanted or external glucose sensor, receives data from said sensor, and uses the data to simplify function and programming of fluid delivery device 10. Various sensors are being developed such as those by Cygnus and MiniMed, both of California. Both implanted and external sensors are becoming available. These sensors could be coupled with wireless communication devices to communicate with the DCA 500, or the DCA 500 may include the necessary communication mechanisms to directly obtain the information made available by these glucose sensing technologies. The DCA 500 and/or the electronic microcontroller 50 may include algorithms to calculate blood glucose readings from the information obtained from the separate blood glucose sensor or sensor assembly, or the information may already be in standardized blood glucose format.

If the fluid delivery device 10 processes the information and adjusts programming automatically, the fluid delivery device is using the DCA 500 to close the loop in its own fluid delivery algorithm, and fluid delivery device 10 is effectively acting as an artificial organ such as a pancreas in the case of insulin delivery. Alternatively, some user intervention may be included to confirm acceptability of the readings prior to some or all programming modifications. Various companies are developing implanted glucose sensors which work in conjunction with an external reader, sometimes utilizing light sources, to retrieve information corresponding to blood glucose levels. The DCA 500 can take the place of the external reader, driving and or receiving information from the sensor, and reporting the information to the user and or using the information to adjust or otherwise modifying the programming of fluid delivery device 10. In the configuration of fluid delivery device 10 of FIG. 9, the reusable assembly 700 is located on the bottom when the device is attached to the skin of the patient via adhesive attachment means, specifically housing adhesive layer 201. In this configuration, the DCA 500 can be located in direct or near contact with the patient's skin, to minimize the distance between the DCA 500 and an implanted or external sensor or device.

Alternatively, if the disposable assembly 800 is located closer to the patient's skin, as has been described in earlier figures, the DCA 500 may be located in the disposable assembly 800, although this is less preferred due to cost, or the DCA 500 may protrude out of the reusable assembly 700 through an opening or next to housing 802, to be closer to a mating device or implanted sensor. Glucose sensing is a preferred use of the DCA 500, however various other diagnostic data can be useful, especially those that correlate to an amount of liquid medication to be infused. Information can include blood analysis, pressure measurements, electrocardiogram or respiration data or other physiologic information. The incorporation of the DCA 500 into the reusable assembly 700 of fluid delivery device 10 can reduce the need for a separate reader or interpretive device, as well as simplifying use or interpretation of the diagnostic data for the patient or clinician.

In the device of FIG. 9, the reusable assembly 700 is attached to the patient's skin via the housing adhesive layer 201. The reusable assembly 700 can be attached to the patient's skin, after which disposable assembly 800 is attached to reusable assembly 700, or the two assemblies can be first attached to each other, and the completed device, fluid delivery device 10 attached to the patient's skin. The housing adhesive layer 201 can include multiple, individually exposable layers of adhesive to improve repeated attachment of the reusable assembly 700, or the housing adhesive layer 201 may be removable and replaceable by the user.

FIGS. 10a and 10b illustrate operation of an automatic fluid path occluder 870 of the device 10 of FIG. 9. The fluid path occluder 870 automatically occludes fluid flow through the flexible fluid transport tube 77 when the disposable assembly 800 is unattached to the reusable assembly 700, as shown in FIGS. 9 and 10a. The fluid path occluder 870 automatically releases the flexible fluid transport tube 77 when the disposable assembly 800 is attached to reusable assembly 700, as shown in FIG. 10b.

The fluid path occluder 870 includes a pivoting member 871 that is pivotally mounted in the disposable housing 802 at a pivot point 872. The pivoting member 871 is biased by a spring 873, which causes the pivoting member 871 to pivot and compress the fluid transport tube 77 against a housing occluding surface 874 with sufficient force to prevent fluid from exiting the disposable assembly 800, as shown in FIGS. 9 and 10a.

A projection 702 from the reusable housing 702 passes through an opening in housing 802, as shown in FIG. 10b, and pivots the pivoting member 871 against the bias of the spring 873. The pivoting member 871 moves away from housing occluding surface 874 and allows the fluid transport tube 77 to open and allow fluid flow through the tube 77. The function of this occluding assembly 870 prevents inadvertent fluid flow whenever the disposable assembly 800 is not properly attached to the reusable assembly 700. When the disposable assembly 800 is subsequently detached from the reusable assembly 700, the housing projecting member 706 is withdraw, such that the occluder spring 873 can bias the pivoting member 871 to close the fluid transport tube 77 against the housing occluding surface 874.

Alternative to the mechanical occluder system shown in FIG. 9, an electrically activated occluding mechanism could be incorporated, wherein an electrical connection is completed or opened via attachment and detachment of disposable assembly 800 to reusable assembly 700 such that when the assemblies are separate or detached, the flow path of disposable assembly 800 is occluded, yet when the two assemblies are connected, an electrical connection causes the occlusion means to deactivate. It should also be appreciated that while the occlusion mechanism of FIG. 9 includes a single occlusion point, additional occlusion points could be included via the same lever mechanism or additional lever mechanisms for enhanced occlusion.

Figure 11:
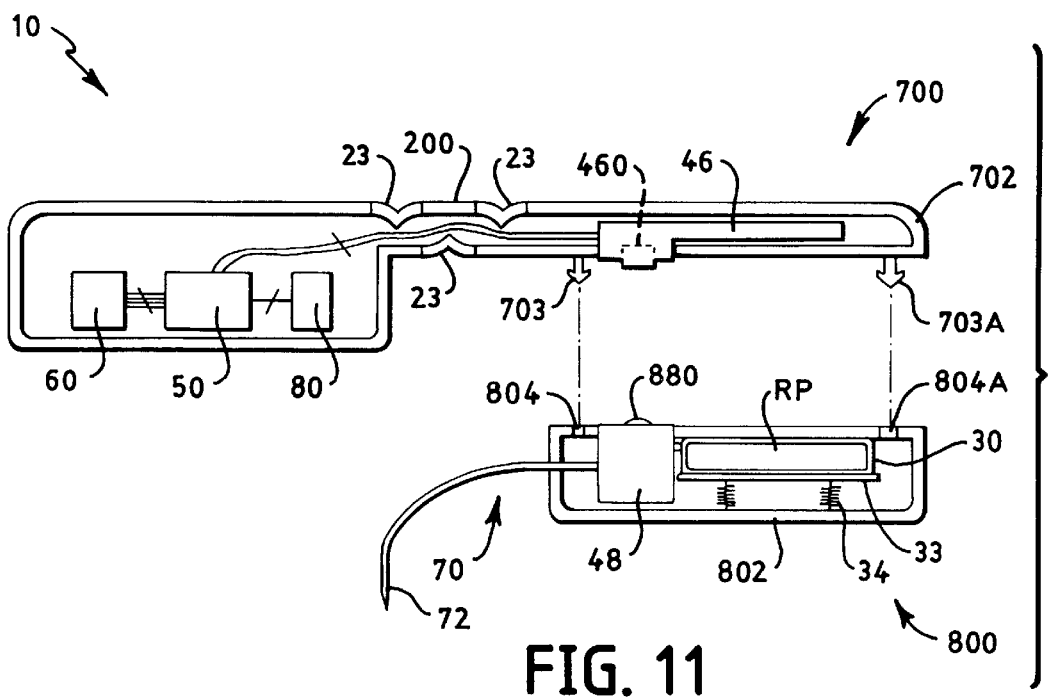
FIG. 11 is an exploded sectional side view of another embodiment of the modular fluid delivery device of the present invention.

FIG. 11 shows a further exemplary embodiment of a fluid delivery device 10 constructed in accordance with the present invention. The device of FIG. 11 is similar to the device of FIGS. 1 and 2, such that similar elements have the same reference numeral.

The reusable assembly 700 of the device of FIG. 11 includes a flexible pivoting section that attaches to the disposable assembly 800. The flexible pivoting section of the housing 702 has hinged sections 23 to permit flexing. Alternatively, all of the housing 702 may be made of flexible material, such as a silicone elastomer.

The reusable assembly 800 of the device of FIG. 7 has a cross sectional area approximately twice as large as the cross sectional area of the disposable assembly 800 as perceived from a top view. When connected, disposable assembly 800 attached to one half portion of the cross sectional area of the reusable assembly 700 as is shown in FIG. 7. If the fluid delivery device 10, with reusable assembly 700 and disposable assembly 800 attached, is strapped or adhesively attached to the body of the patient, attachment means not shown, it may be desirable to allow flexing of portions of the device to provide comfort to the patient. Additionally or alternatively, disposable assembly 800 may have a larger cross sectional area than the reusable assembly. Also, additionally or alternatively, disposable assembly 800 may include flexible sections along its housing housing 802, or housing 802 may be flexible. Flexible materials may consist of silicone elastomers, or other durable yet flexible materials.

The disposable assembly 800 includes the reservoir 30, which is a compressible bladder containing a therapeutic fluid, such as insulin, and a compression member 33 that contacts a majority of the cross section of the reservoir and pressurizes the fluid within reservoir 30 via a force applied from one or more springs 34. An alternative to the compression springs 34 is to include the reservoir 30 in a sealed compartment formed in the housing 802 and fill the sealed compartment with pressurized gas in order to pressurize the reservoir.

Figure 12:
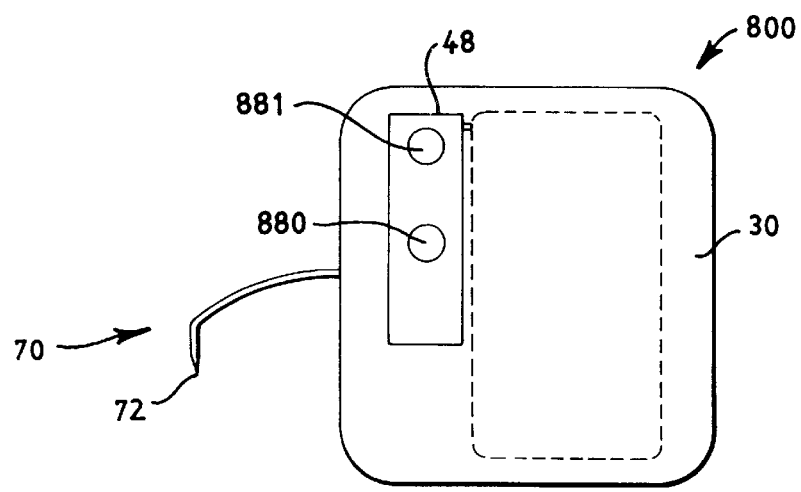
FIG. 12 is a top plan view of a disposable module of the device of FIG. 11.

The disposable assembly 800 also includes the metering portion 48, which is activated by the meter control portion 46 of the reusable assembly 700. When the two assemblies are properly attached, the meter control portion 46 is aligned to provide a controlling function of the metering portion 48. As also shown in FIG. 12, the metering portion 48 includes two valves 880, 881 that are aligned with corresponding actuators 460 (only one of two actuators is viewable) of the meter control portion 46 of the dispenser 40 when the disposable assembly 800 is attached to the reusable assembly 700.

The valves 880, 881 included in metering portion 48 can be used to selectively fill and evacuate a fluid accumulator (not shown) within the metering portion 48, causing fixed pulse volumes PV of fluid to flow to the exit port assembly 70 and out the distal tip of skin penetrating cannula 72. Alternatively, the valves 880, 881 can cause positive displacement of fluid, with multiple valves incorporated for safety purposes. The corresponding actuators 460 are mechanical, but can alternatively be adapted to move the valves via electromagnetic field, temperature, or other controllable forces. The actuators 460 can include a linear or rotary solenoid, piezo actuator or other mechanical actuator construction to mechanically actuate the valves 880, 881.

Various assemblies and products of the present invention may be packaged together, singly or multiply, in kit fashion for practical delivery to the patient, caregiver or other user. For example, the disposable assembly 800 can be packaged in a flexible pouch constructed of a flexible, impermeable material such as Mylar, while the other side is constructed of Tyvek material, supplied by Dupont Corporation, which is slightly porous allowing permeation of sterilizing agents such as ethylene oxide, EtO, while preventing bacteria from contaminating a previously sterilized component. A heat sealing process is used to seal the disposable assembly 800 within disposable assembly pouch. Alternatively, a rigid tray, made from a variety of plastics including PETG or polycarbonate, could replace the Mylar portion, and a TYVEK lid, with adhesive in the contacting portion, could be sealed to the tray, enclosing the disposable assembly 800 and allowing similar sterilization procedures. The Mylar of the pouch or the plastic tray are usually in clear form to allow visualization of the device at the manufacturer and user.

In a preferred embodiment, the disposable assembly 800 includes an integral transcutaneous infusion set, and sterilization of at least the transcutaneous and fluid path portions of the device would be necessary to prevent contaminants from passing through the skin of the patient potentially resulting in an infection or other adverse event. If the disposable assembly 800 does not include an integral transcutaneous infusion set, but rather terminates in a standard fluid connector such as a luer, a standard or customized transcutaneous infusion set could also be included with the packaged disposable assembly 800.

In addition, the disposable assembly 800 can be provided with barcodes to be utilized by various systems for cataloging or otherwise recording information about the disposable assembly 800. For example, the remote controller 100 may include a bar code reader function, and upload the barcode data to perform an initialization function. The information barcode data can be unique for each disposable assembly 800 and include unique disposable assembly identifications or other unique and non-unique information such as manufacturing date, serial number, type of medication preloaded, concentration of medication, physician identification, patient identification, or other clinical or non-clinical information.

The reusable assembly 700 can also be packaged in a flexible pouch, wherein one side of the pouch is constructed of a flexible, impermeable material such as Mylar, while the other side is constructed of Tyvek material, supplied by Dupont Corporation, which is slightly porous allowing permeation of sterilizing agents such as EtO while preventing bacteria from contaminating a previously sterilized component. A heat sealing process is used to seal the reusable assembly 700 within the pouch. Alternatively, a rigid tray, made from a variety of plastics including PETG or polycarbonate, could replace the Mylar portion, and a TYVEK lid, with adhesive in the contacting portion, could be sealed to the tray, enclosing the disposable assembly 800 and allowing similar sterilization procedures. The Mylar of the pouch or the plastic tray are usually in clear form to allow visualization of the device at the manufacturer and user. In the preferred embodiment, the reusable assembly 700 does not need to be sterilized, since its components do not have to make contact with the internal surfaces of the fluid path of disposable assembly 800. While it may be desirable to sterilize reusable assembly 700, it can be avoided to reduce cost. The packaged reusable assembly 700 can also be provided with a barcode.

A therapeutic fluid supply for use with the devices of the present invention may include a glass or plastic vial, and may be filled with various types of one or more liquid medications such as insulin. The therapeutic fluid supply may be loaded, like a cartridge, into a properly designed and adapted fluid delivery device 10, specifically loaded into disposable assembly 800, or the contents of therapeutic fluid supply may be transferred, through interlocking fluid connection or via syringe and needle, into fluid delivery device 10 at a integral injection port. Alternatively, fluid delivery device 10 may be pre-filled with the liquid medication obviating the need for therapeutic fluid supply.

The assemblies 700, 800 can be provided in the form of a kit for a user, and can contain multiple units of one of the assemblies 700, 800 packaged with a single or lesser quantity of another of the assemblies 700, 800. Since the reusable assembly 700 is intended to be used with more than one disposable assembly 800, it is desirable to kit one or more packaged reusable assemblies with two or more packaged disposable assemblies. For example, a kit may include three reusable package assemblies with thirty disposable package assemblies, where each reusable assembly 700 is used for thirty days, and attached to ten different disposable assemblies 800, wherein each of the disposable assemblies is replaced every three days. The entire kit would last for three months or ninety days, and the patient would have backup reusable assemblies 700 and disposable assemblies 800 in case of damage. One or more remote controllers 100 are also included in such a kit, and an appropriate amount of therapeutic fluid supplies for the ninety day period. Certain medications, such as many forms of insulin, need to be refrigerated if stored for an extended period of time. Limitations on amounts of drug used in kits, and storage requirements, may impact amounts and configuration of therapeutic fluid supply within the kit.

In addition to the above components or products, other components may be packaged in the kit. The additional components might include user instructions, batteries for the multi function remote controller 100, multiple batteries for the fluid delivery device 10, especially if the fluid delivery device 10 does not have an integral, non-user insertable battery, syringes, needles, transcutaneous penetration site preparation materials, and other peripheral devices.

If the application of the fluid delivery device 10 and multi function remote controller 100 was treatment of diabetes with insulin infusion, frequent blood glucose measurements would be required as part of the therapy. Blood glucose measuring supplies such as finger prick devices, test strips, diagnostic devices such as glucometers, and other blood glucose measurement accessory devices may be supplied in the kit configuration described above involving multiple delivery device packaged assemblies, each containing fluid delivery device as well as one or more multi function remote controller 100. In the preferred embodiment, some of the blood glucose diagnostic devices, non-disposable, are integrated into remote controller 100. One or more backup multi function remote controllers 100 may be advantageous to be supplied with the kit in case of damage or other inability to use. For diabetes and other therapies, diagnostic devices other than a glucometer may be desirable to be included in the kit. Such a diagnostic device may be used to gather clinical information from the patient regarding the infusion therapy. The multi function remote controller 100 may communicate with the separate diagnostic device and potentially control it as well via its wireless communication element and a receiving element in the diagnostic device. To receive information from the diagnostic device, electronic information could be transferred via wireless communications previously described, or by direct manual electrical connection between the multi function remote controller 100 and the diagnostic device, all not shown.

The fluid delivery device 10 of the present invention is intended to be low cost, and while disposable assembly 800 is disposable, reusable assembly 700 is intended to be of limited life. It may be advantageous for one or more of the components to be biodegradable, since replacement of the disposable assembly 800 every two to five days has many advantages, it would also generate a fair amount of waste. The fluid delivery device 10 may include a preinstalled battery as its power supply 80. In order to prevent the battery from powering the electronics of fluid delivery device 10 before its intended use, a mechanical switch may be included, connecting the battery contacts to the electronics prior to programming with the remote controller 100. A simplistic version of the switch design may be an insulating material between the battery contacts of power supply 80 and the electrical connection to the electronic microcontroller 50. The insulating material could be designed to protrude through housing 20, and be removable by the user, not shown. The user could pull the insulating material and remove it, simultaneously connecting the battery contacts with the electrical connection to the electronic microcontroller. Alternatively, the connection of reusable assembly 700 to disposable assembly 800 could activate or otherwise connect a power supply located in either or both assemblies.

The fluid delivery device 10, specifically the reservoir 30 of disposable assembly 800, of the present invention may be filled with the therapeutic fluid by the device manufacturer, a pharmaceutical company, or another manufacturer prior to its shipment to the hospital, pharmacy or patient. Certain drugs require refrigeration or other special environmental conditions, requiring the pre-filled fluid delivery device to be refrigerated or otherwise handled to meet special requirements. Insulin is a drug that requires refrigeration if it is to be stored for a prolonged period of time. Hoechst, of Frankfurt Germany, is developing insulin that is stable at higher temperatures. Drugs that are stable at room temperature, such as the developmental insulin of Hoechst, allow simple filling and handling of the fluid delivery device 10, greatly simplifying the requirements for the patient.

The fluid delivery device 10 of the present invention includes disposable assembly 800 and reusable assembly 700. Each embodiment may additionally include, either in disposable assembly 800 or reusable assembly 700 various sensors or fluid path components including but not limited to: air bubble detectors, bubble removers, flow sensors, occlusion sensors, pressure sensors, leak detectors, volume transducers such as that disclosed in U.S. Pat. No. 5,575,310 to Kamen et al, voltage and current level detectors, particle filters, position sensors, linear and rotary encoders, and other sensors and fluid path components.

The fluid delivery device 10 of the present invention may include means of adhesively attaching fluid delivery device 10 to the skin of the patient. Alternatively, the device could be worn in a harness strapping it close to the patient's skin, or in a purse or pocket. Preferably, the fluid delivery device is located close to the patient's skin during use, limiting the fluid path between the dispensing means and the transcutaneous entry site. In the preferred embodiment, the disposable assembly 800 includes adhesive attachment means, and is placed on the skin of the patient, with the reusable assembly 700 located on top. Alternative arrangements include having the reusable assembly 700 on top, or the two assemblies side by side. The overall size of fluid delivery device 10 is small, allowing comfort when attached or strapped to the patient's skin. The housing or portions of housings that make up reusable assembly 700 or disposable assembly 800, or both, may be made of flexible material such as silicone elastomer, to allow flexing and enhance comfort.

The remote controller 100 of the present invention is used to program and otherwise control the fluid delivery device 10 including reusable assembly 700 and disposable assembly 800. Remote controller 100 can download information to initiate or change continuous flow parameters, start, stop, change or preprogram a bolus delivery. The remote controller 100 preferably includes an alarm transducer that can be an audio alarm, vibrational or tactile alarm or both. Conditions that cause an alarm to sound can include an occlusion or under infusion of liquid therapeutic, over infusion of liquid therapeutic, leak, malfunction of any component of reusable assembly 700, disposable assembly 800 or remote controller 100, transcutaneous cannula out of position, proximity between remote controller 100 and fluid delivery device 10 exceeded predetermined maximum, and various other alarm conditions. An alarm transducer can be included in the fluid delivery device 10 as well, potentially in disposable assembly 800 but preferably in reusable assembly 700. If cost, size or power constraints limit the ability to include an alarm transducer in fluid delivery device 10, it is more important that remote controller 100 include an alarm transducer, and that the proximity alarm described in detail hereabove, be employed.

Various forms of attachment means have been described in this application, all versions providing means of first attaching the disposable assembly 800 to the reusable assembly 700 and then detaching the two assemblies, without damaging reusable assembly 700. Means included projecting members that mate with receiving holes providing a snap fit, concentric threads, adhesives and other means. Alignment pegs that assist in orienting the disposable assembly 800 to the reusable assembly 700 prior to attachment have also been described. Attachment means can provide additional functions such as activating or deactivating mechanisms found in the other assembly, providing electrical power or signal connections, or other functions. It may be desirable to include a switch which is opened or closed when reusable assembly 700 is attached to disposable assembly 800. The switch could control a signal that is fed to electronic microcontroller 50 of reusable assembly 700. Certain user functions, such as programming, may be tied to requiring the two assemblies to be attached or not attached to complete the step. The fluid delivery device 10, communicating through remote controller 100 can force the patient to follow a specific order in attaching the two assemblies, programming the device, etc.

Various models of reusable assemblies 700 may be designed, for specific functions such as treatment of diabetes. It may be desirable to customize or code the shape of the attachment means to insure that only an acceptable disposable assembly 800, such as one filled with insulin, is attached to the appropriate reusable assembly 800, such as one including programming specific to treatment of diabetes. The customized attachment means may be very useful in situations where disposable assembly 800 is pre-filled with liquid therapeutic by the manufacturer. Other uses of customized attachment means mating appropriate disposable assemblies 800 with the proper reusable assemblies 700 could be employed to simplify use for the clinician, clinic and user and avoid undesired mismatches.

Various methods of using the fluid delivery device 10 are included in the present invention and described above. The method of attaching the reusable assembly 700 to the disposable assembly 800 to create fluid delivery device 10, the method of programming the reusable assembly 700 or fluid delivery device 10 with remote programmer 100 as well as the method of attachment and use of the peripheral devices including transcutaneous infusion sets and diagnostic devices such as glucometers are described. Also relevant is the ability to update the internal programming of either the fluid delivery device 10 or the remote controller 100 by the corresponding device. Methods of filling the fluid delivery device 10 with therapeutic fluid during the manufacturing process as well as by the user have been described. Methods of programming the fluid delivery device with remote controller 100 have been described. Methods of piercing the skin with transcutaneous entry means in order to place the fluid exit the device to a site within the patient's body have been described. Methods and timing of sterilization and packaging of part or all of the disposable assembly 800 and or reusable assembly 700, and therapeutic fluid 250 have also been described. Many of the methods previously mentioned can be linked to each other with requirements of specific orders to be followed prior to initiating or completing another step.

Although exemplary embodiments of the invention have been shown and described, many changes, modifications and substitutions may be made by those having ordinary skill in the art without necessarily departing from the spirit and scope of this invention. For example, the fluid delivery device of this invention is intended to be low cost, light weight, simple to use and potentially disposable by removing a majority of the user interface, including electromechanical switches, from the fluid delivery device, and including a separate controller to replace those functions. The disposable assembly 800 is designed to be further cost reduced by placing various components into the reusable assembly 700 such as the microprocessor and associated electronics, wireless communication, and meter control portion which mate with a metering portion still included in disposable assembly 800. While various means of reservoir construction, pressurization means, fluid pumping means, fluid metering means, transcutaneous delivery, electronic control and wireless communications have been discussed in this application, alternatives to each of these areas can be made without departing from the spirit of the invention.

In addition, where this patent application has listed the steps of a method or procedure in a specific order, it may be possible (or even expedient in certain circumstances) to change the order in which some steps are performed, and it is intended that the particular steps of the method or procedure claims set forth herebelow not be construed as being order-specific unless such order specificity is expressly stated in the claim.

What is claimed is:

1. A device for delivering fluid comprising:
   A) a disposable assembly including,
      an exit port assembly,
      a metering portion of a dispenser for controlling fluid flow to the exit port assembly, and
      a housing containing the exit port assembly and the metering portion of the dispenser;
   B) a reusable assembly including,
      a control portion of the dispenser adapted to control the metering portion of the dispenser upon attachment of the reusable assembly and the disposable assembly,
      a local processor connected to the dispenser and programmed to cause fluid flow to the exit port assembly through the dispenser based upon flow instructions,
      a local wireless communication element connected to the local processor for receiving flow instructions from a remote wireless device, and
      a housing containing the control portion of the dispenser, the controller and the local wireless communication element and adapted to removably attach to the housing of the disposable assembly; and
   C) a power source contained in the disposable assembly for providing power to the reusable assembly upon attachment of the reusable assembly and the disposable assembly.

2. A device according to claim 1, further comprising an adhesive on an outwardly facing surface of at least one of the housings for securing the device to skin of a patient.

3. A device according to claim 1, wherein the housing of the disposable assembly is flexible.

4. A device according to claim 1, wherein the housing of the reusable assembly is flexible.

5. A device according to claim 1, wherein the housing of the disposable assembly is constructed of biodegradable materials.

6. A device according to claim 1, wherein the wireless Communication element communicates through radio frequency signals.

7. A device according to claim 1, wherein the housing of the reusable assembly further contains a power supply connected to the local processor.

8. A device according to claim 7, wherein the power supply of the reusable assembly is non-replacable.

9. A device according to claim 1, wherein the power supply of the disposable assembly is non-replacable.

10. A device according to claim 1, wherein the power supply of the disposable assembly is a battery.

11. The fluid device of claim 1, wherein the power supply of the disposable assembly is electrically connected to the reusable assembly through conductive contacts when the disposable assembly and reusable assembly are attached.

12. A device according to claim 11, wherein the conductive contacts are spring loaded.

13. A device according to claim 1, wherein the reusable assembly includes at least one electrical connector connected to the processor and adapted to mate with an electrical connector of the reusable assembly when the disposable assembly is attached to the reusable assembly, and wherein the electrical connector of the reusable assembly is connected to the power supply.

14. A device according to claim 1, wherein the power supply contains a predetermined amount of energy.

15. A device according to claim 1, wherein the processor includes an electrical energy storage device to power memory storage devices of the processor.

16. A device according to claim 1, wherein the housings are removably attachable with attachment projecting members extending from one of the housing of the reusable assembly and the housing of the disposable assembly, and corresponding attachment receiving holes in the other of the reusable assembly and the disposable assembly.

17. A device according to claim 16, wherein the attachment projecting members and the attachment receiving holes are provided in one of at least two shapes and at least two sizes, to cause a specific alignment when the reusable assembly is attached to the disposable assembly.

18. A device according to claim 1, further comprising alignment projecting members extending from one of the disposable and the reusable assemblies which mate with alignment receiving boles in the other of the disposable and the reusable assemblies.

19. A device according to claim 1, wherein the housings are removably attachable with screw threads.

20. A device according to claim 1, wherein the housings are removably attachable with adhesive.

21. A device according to claim 1, further comprising a reservoir within the housing of the disposable assembly, and the metering portion of the dispenser controls fluid flow from the reservoir to the exit port assembly.

22. A device according to claim 21, wherein the reservoir contains a therapeutic fluid.

23. A device according to claim 21, wherein the disposable assembly further comprising a fill port connected to the reservoir.

24. A device according to claim 21, wherein the reservoir is pressurized.

25. A device according to claim 21, wherein the reservoir contains a therapeutic fluid comprising at least one of insulin, antibiotics, nutritional fluids, TPN, analgesics, morphine, hormones or hormonal drugs, gene therapy drugs, anticoagulants, analgesics, cardiovascular medications, AZT or chemotherapeutics.

26. A device according to claim 21, wherein the reservoir contains a therapeutic fluid for treating at least one of diabetes, cardiovascular disease, pain, chronic pain, cancer, AIDS, neurological diseases, Alzheimer's, ALS, Hepatitis, Parkinson's Disease or Spasticity.

27. A device according to claim 21, wherein the reservoir is made of an elastic material.

28. A device according to claim 21, wherein the reservoir is pre-filled.

29. A device according to claim 21, wherein housing of the disposable assembly includes vent ports adjacent the reservoir.

30. A device according to claim 21, wherein the reservoir is pre-filled with a predetermined volume of fluid.

31. A device according to claim 21, wherein the reusable assembly applies force on the reservoir in the disposable assembly upon attachment of the reusable and the disposable assemblies.

32. A device according to claim 1, wherein the exit port assembly includes a luer connector.

33. A device according to claim 1, wherein the exit port assembly includes a cannula.

34. A device according to claim 1, wherein the disposable assembly further comprises a flow prevention assembly adapted close the exit port assembly prior to attachment of the disposable assembly and the reusable assembly.

35. A device according to claim 1, wherein the flow prevention assembly includes a pivotal member biased against the exit port assembly, and the reusable assembly includes a projecting member adapted to pivot the pivotal member away from the exit port assembly upon attachment of the disposable assembly and the reusable assembly.

36. A device according to claim 1, wherein the metering portion of the dispenser includes a pump mechanism.

37. A device according to claim 36, wherein the control portion of the dispenser includes a drive mechanism engagable with the pump mechanism of the metering portion upon attachment of the disposable assembly and the reusable assembly.

38. A device according to claim 36, wherein the pump mechanism is a rotary peristaltic.

39. A device according to claim 36, wherein the pump mechanism is a linear peristaltic.

40. A device according to claim 1, wherein the metering portion of the dispenser includes at least one valve.

41. A device according to claim 40, wherein the control portion of the dispenser includes a valve actuator engagable with the valve of the metering portion upon attachment of the disposable assembly and the reusable assembly.

42. A device according to claim 41, wherein the valve actuator is a piezoelectric actuators.

43. A device according to claim 41, wherein the valve actuator is a solenoid actuators.

44. A device according to claim 41, wherein the valve actuator is a thermal actuator.

45. A device according to claim 1, wherein the metering portion of the dispenser includes at least one pulse chamber having a predetermined volume.

46. A device according to claim 45, wherein the metering portion of the dispenser includes at least one diaphragm positioned against the pulse chamber.

47. A device according to claim 1, wherein the disposable assembly further includes at least one sensor.

48. A device according to claim 47, wherein the sensor monitors at least one of pressure, flow, presence of fluid, presence of air, resistance, electrical current or electrical voltage.

49. A device according to claim 47, wherein the reusable assembly includes at least one sensor monitor adapted to communicate with the sensor of the disposable assembly.

50. A device according to claim 49, wherein the assemblies include mating electrical connectors adapted to connect the sensor monitor to the sensor when the disposable assembly is attached to the reusable assembly.

51. A device according to claim 1, wherein the reusable assembly further comprises at least one sensor adapted to detect a performance parameter of the disposable assembly.

52. A device according to claim 51, wherein the sensor of the reusable assembly makes physical contact with a portion of the disposable assembly when the disposable assembly is attached to the reusable assembly.

53. A device according to claim 52, wherein the sensor assembly makes physical contact with a fluid path component of the disposable assembly.

54. A device according to claim 1, wherein the housings are free of user input components for providing flow instructions to the local processor.

55. A system including a fluid delivery device according to claim 1, and further comprising a remote control device separate from the fluid delivery device and including:

a remote processor;

user interface components connected to the remote processor for allowing a user to provide flow instructions to the remote processor; and a transmitter connected to the remote processor for transmuting the flow instructions to the wireless communication element of the fluid delivery device.

56. A system including a fluid delivery device according to claim 1, and further comprising a remote control device separate from the fluid delivery device and including:

a remote processor;

user output components connected to the remote processor or allowing a user to receive flow information; and a receiver connected to the remote processor for receiving the flow information from the wireless communication element of the fluid delivery device.

* * * * *

UNITED STATES PATENT AND TRADEMARK OFFICE
CERTIFICATE OF CORRECTION

PATENT NO. : 6,749,587 B2
DATED : June 15, 2004
INVENTOR(S) : J. Christopher Flaherty It is certified that error appears in the above-identified patent and that said Letters Patent is hereby corrected as shown below:

<u>Column 28,</u>
Line 33, before "allowing", delete "or", and insert therefor -- for --.

Signed and Sealed this

Thirty-first Day of August, 2004

JON W. DUDAS
*Director of the United States Patent and Trademark Office*

UNITED STATES PATENT AND TRADEMARK OFFICE
CERTIFICATE OF CORRECTION

PATENT NO. : 6,749,587 B2
DATED : June 15, 2004
INVENTOR(S) : J. Christopher Flaherty It is certified that error appears in the above-identified patent and that said Letters Patent is hereby corrected as shown below:

<u>Title page,</u>
Item [60], insert:
-- Related U.S. Application Data
Provisional application No. 60/270,970, filed Feb. 22, 2001. --

Signed and Sealed this

Fifteenth Day of March, 2005

JON W. DUDAS
*Director of the United States Patent and Trademark Office*